(12) United States Patent
Rasmussen et al.

(10) Patent No.: US 9,546,941 B2
(45) Date of Patent: Jan. 17, 2017

(54) METHOD AND SYSTEM FOR ESTIMATING THE SPECIFIC GRAVITY OF AN UNKNOWN FUEL SOURCE IN A MULTI-FUEL ENGINE

(71) Applicant: Caterpillar Inc., Peoria, IL (US)

(72) Inventors: Jason Rasmussen, Hopewell, IL (US); Brett Zook, Cutler, IN (US); Baoyang Deng, Edwards, IL (US); Arvind Sivasubramanian, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 77 days.

(21) Appl. No.: 14/703,587

(22) Filed: May 4, 2015

(65) Prior Publication Data

US 2016/0327464 A1  Nov. 10, 2016

(51) Int. Cl.
| F02D 19/00 | (2006.01) |
| G01N 9/26 | (2006.01) |
| F02B 43/10 | (2006.01) |
| F02D 19/02 | (2006.01) |
| G01N 9/36 | (2006.01) |
| G01N 9/00 | (2006.01) |

(52) U.S. Cl.
CPC ............... *G01N 9/266* (2013.01); *F02B 43/10* (2013.01); *F02D 19/026* (2013.01); *F02D 19/029* (2013.01); *F02D 2200/025* (2013.01); *F02D 2200/0611* (2013.01); *F02D 2200/0612* (2013.01); *G01N 9/26* (2013.01); *G01N 9/36* (2013.01); *G01N 2009/004* (2013.01)

(58) Field of Classification Search
CPC ............ G01N 9/266; G01N 9/26; G01N 9/36; G01N 2009/004; F02B 43/10; F02B 2043/103; F02D 2200/025; F02D 2200/0611; F02D 2200/0612
See application file for complete search history.

(56) References Cited

U.S. PATENT DOCUMENTS

| 4,246,773 A * | 1/1981 | Haruta ................. G01N 29/024 73/24.01 |
| 4,517,928 A * | 5/1985 | Wolters ............... F02D 19/0605 123/27 GE |
| 5,526,645 A * | 6/1996 | Kaiser ................... F02D 19/105 123/564 |

(Continued)

FOREIGN PATENT DOCUMENTS

| DE | 102010045593 A1 | 3/2012 |
| JP | H02233872 A1 | 9/1990 |
| JP | 5141219 B2 | 2/2013 |

*Primary Examiner* — Hieu T Vo
*Assistant Examiner* — Sherman Manley
(74) *Attorney, Agent, or Firm* — Miller, Matthias & Hull LLP

(57) ABSTRACT

A method for estimating a specific gravity of a gaseous fuel is described. The gaseous fuel may power an engine and the engine may include a cylinder, a gas valve configured to supply an intake port of the cylinder with the gaseous fuel, a gas rail configured to deliver the gaseous fuel to the gas valve, and a microprocessor adapted to perform the method. The method may comprise establishing a pressure wave in the gas rail by opening and closing the gas valve, wherein the pressure wave travels at the speed of sound in the gaseous fuel. The method may further comprise determining a frequency of the pressure wave in the gas rail, and estimating the specific gravity of the gaseous fuel based on the frequency of the pressure wave.

20 Claims, 11 Drawing Sheets

(56) References Cited

U.S. PATENT DOCUMENTS

| | | | | |
|---|---|---|---|---|
| 5,622,053 | A * | 4/1997 | Freen | F02B 33/44 123/299 |
| 5,697,346 | A * | 12/1997 | Beck | F02D 19/061 123/1 A |
| 5,890,459 | A * | 4/1999 | Hedrick | F02B 69/02 123/27 GE |
| 6,003,478 | A * | 12/1999 | Huber | F02B 7/06 123/27 GE |
| 6,055,963 | A | 5/2000 | Brown et al. | |
| 6,474,137 | B1 * | 11/2002 | Hammond | G01N 9/24 73/24.01 |
| 6,481,288 | B1 * | 11/2002 | Humphrey | G01H 5/00 73/579 |
| 7,107,851 | B2 * | 9/2006 | Owen | G01H 5/00 702/54 |
| 7,316,151 | B2 | 1/2008 | Sivaraman | |
| 8,042,384 | B2 * | 10/2011 | Bailey | F02D 19/0628 73/114.38 |
| 8,301,359 | B1 | 10/2012 | Sagar et al. | |
| 9,133,782 | B1 * | 9/2015 | Convisser | F02D 41/0025 |
| 2010/0231371 | A1 | 9/2010 | Arakawa et al. | |
| 2011/0166770 | A1 * | 7/2011 | Deguchi | F02D 41/0025 701/103 |
| 2013/0233056 | A1 * | 9/2013 | Ishiguro | G01N 29/024 73/30.01 |
| 2014/0360471 | A1 * | 12/2014 | Sugiyama | F02D 41/062 123/457 |
| 2014/0366839 | A1 | 12/2014 | Sivasubramanian et al. | |
| 2014/0366840 | A1 | 12/2014 | Sivasubramanian et al. | |

\* cited by examiner

_US 9,546,941 B2_

METHOD AND SYSTEM FOR ESTIMATING THE SPECIFIC GRAVITY OF AN UNKNOWN FUEL SOURCE IN A MULTI-FUEL ENGINE

TECHNICAL FIELD

The present disclosure generally relates to multi-fuel engines powered by a fuel source having unknown properties and, more specifically, to methods and systems for estimating the specific gravity of a fuel source having unknown properties.

BACKGROUND

A multi-fuel engine is an engine designed to combust multiple types of fuel with air in its operation. Multi-fuel engines may be desirable where cheaper and cleaner fuel sources, such as natural gas, are available as a primary fuel source but a secondary fuel (e.g., diesel) is desired for performance reasons or as a backup in the event of depletion of the primary fuel source. A dual fuel engine, for example, may be designed to run on either or both of a primary fuel source and a secondary fuel source at a range of relative ratios depending on performance requirements and availability of the fuel sources. In one implementation of a dual fuel engine, the engine may primarily run on natural gas with a pilot amount of diesel fuel being used as an ignition source.

Multi-fuel engines, such as dual fuel engines, require precise knowledge of the properties each of the fuel types in order to regulate various engine performance parameters such as the fuel flow rate and the engine air/fuel ratio, or lambda ($\lambda$). However, some gaseous fuel sources, such as natural gas, may have a composition that is unknown and/or changing with time. For example, natural gas may include various species such as methane ($CH_4$), ethane ($C_2H_6$), propane ($C_3H_8$), and gases (e.g., nitrogen ($N_2$) and carbon dioxide ($CO_2$)) in various relative percentages that may continuously change with time. With the composition of natural gas being unknown, the physical properties (e.g., specific gravity, lower heating value (LHV), etc.) of the fuel will be unknown as well. For some applications, it may be cost-prohibitive to employ separate analytical techniques to continuously monitor the composition and properties of the natural gas fuel as it is being supplied to the engine. When running on one or more fuel sources with unknown properties, the performance of a multi-fuel engine may suffer. For example, it may be difficult or impossible to carefully regulate the fuel flow rate and $\lambda$ if the specific gravity of one or more of the fuel sources is unknown.

U.S. Patent Application Publication Number 2013/0233056 teaches an analytical device that is capable of measuring the specific gravity of a gas fuel, such as natural gas, in a pipeline. The device disclosed therein is configured to measure the specific gravity of the gas fuel on the basis of the refractive index of the gas fuel and the speed of sound of the gas fuel. While effective, further improvements that enable property measurements of unknown fuel compositions are still wanting.

Clearly, there is a need for improved methods and systems capable of monitoring fuel properties in engines operating with a fuel source having an unknown composition.

SUMMARY

In accordance with one aspect of the present disclosure, a method for estimating a specific gravity of a gaseous fuel is disclosed. The gaseous fuel may power an engine and the engine may include a cylinder, a gas valve configured to supply an intake port of the cylinder with the gaseous fuel, a gas rail configured to deliver the gaseous fuel to the gas valve, and a microprocessor adapted to perform the method. The method may comprise establishing a pressure wave in the gas rail by opening and closing the gas valve, wherein the pressure wave travels at a speed of sound in the gaseous fuel. The method may further comprise determining a frequency of the pressure wave in the gas rail, and estimating the specific gravity of the gaseous fuel based on the frequency of the pressure wave.

In accordance with another aspect of the present disclosure, an engine powered by a gaseous fuel having an unknown specific gravity is disclosed. The engine may comprise at least one cylinder having a combustion chamber disposed therein, a piston positioned for displacement within the cylinder, an intake port configured to deliver a mixture of air and the gaseous fuel to the cylinder, a gas valve configured to regulate a gas mass flow into the cylinder, and a gas rail configured to supply the gas valve with the gaseous fuel. The gas valve may be configured to generate a pressure wave in the gas rail when the gas valve is opened and closed. In addition, the engine may further comprise a pressure sensor in the gas rail configured to detect the pressure wave, and a specific gravity estimation module configured to determine a frequency of the pressure wave detected by the pressure sensor, and to estimate the specific gravity of the gaseous fuel based on the frequency of the pressure wave.

In accordance with another aspect of the present disclosure, a method for estimating a specific gravity of a gaseous fuel is disclosed. The gaseous fuel may power a multi-fuel engine configured to run on at least the gaseous fuel and diesel fuel. The engine may include a plurality of cylinders, an intake port associated with each one of the cylinders, a gas valve associated with each one of the intake ports and configured to supply the intake port with the gaseous fuel, a gas rail configured to supply the gas valves with the gaseous fuel, and a microprocessor adapted to perform the method. The method may comprise running one of the cylinders in gas mode in which the cylinder is supplied with the gaseous fuel as a primary fuel source, and running the remaining cylinders in diesel mode in which the diesel fuel is used as a sole fuel source. The method may further comprise establishing a pressure wave in the gas rail by opening and closing the gas valve associated with the cylinder running in gas mode, and the pressure wave may travel at a speed of sound in the gaseous fuel. In addition, the method may further comprise determining a frequency of the pressure wave in the gas rail, and estimating the specific gravity of the gaseous fuel based on the frequency of the pressure wave.

These and other aspects and features of the present disclosure will be more readily understood when read in conjunction with the accompanying drawings.

It should be understood that the drawings are not necessarily drawn to scale and that the disclosed embodiments are sometimes illustrated schematically and in partial views. It is to be further appreciated that the following detailed description is merely exemplary in nature and is not intended to limit the invention or the application and uses thereof. In this regard, it is to be additionally appreciated that the described embodiment is not limited to use with a particular type of engine or type of fuel. Hence, although the present disclosure is, for convenience of explanation, depicted and described as certain illustrative embodiments, it will be appreciated that it can be implemented in various other types of embodiments and in various other systems and environments.

DETAILED DESCRIPTION

Figure 1:
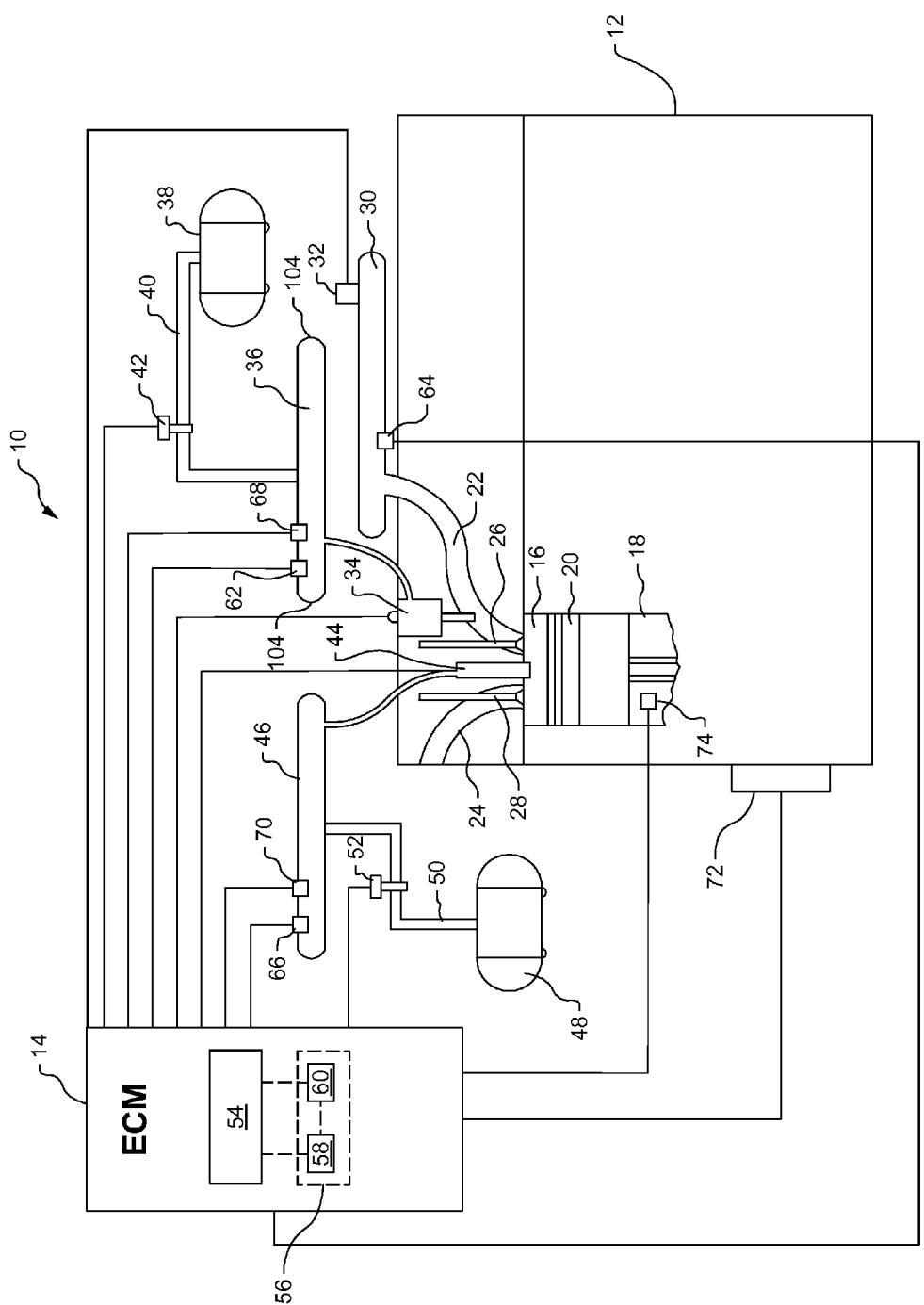
FIG. 1 is a schematic view of an exemplary multi-fuel engine system capable of running on a gaseous fuel source having an unknown composition and specific gravity, in accordance with the present disclosure.

Referring now to the drawings, and with specific reference to FIG. 1, an exemplary engine system 10 constructed in accordance with the present disclosure is shown. The engine system 10 may include an internal combustion engine 12 and an electronic control module (ECM) 14 which may control the flow of air and fuel into the engine 12 as well as other functions. Two or more different types of fuel may provide power to the engine 12. One of the fuel sources may have an unknown composition or a composition that is changing with time, as well as unknown physical properties such as specific gravity (SG) and lower heating value (LHV). For example, the engine 12 may be a dual fuel engine that is powered by a primary gaseous fuel source having an unknown composition, such as natural gas, and a secondary liquid fuel source, such as diesel fuel. In this case, the engine 12 may be powered by various relative percentages of the gaseous fuel and the diesel fuel. However, the engine 12 may be configured to run on all diesel fuel such as when the gaseous fuel supply is low. Although the following description is largely focused on dual fuel engines powered by a gaseous fuel source and diesel fuel, it will be understood that the teachings of the present disclosure may be implemented in various types of engines in which one of the fuel sources has an unknown composition and unknown physical properties.

The engine 12 may include a combustion chamber 16 disposed in a cylinder 18, a piston 20 positioned for displacement within the cylinder 18, an intake port 22 configured to supply the combustion chamber 16 with a mixture of air and gaseous fuel (e.g., natural gas), an exhaust port 24, and an intake valve 26 and an exhaust valve 28 for regulating fluid communication between the cylinder 18 and the intake port 22 and the exhaust port 24, respectively.

The intake port 22 may receive air from an air intake manifold 30 which may include an airflow controller 32 for regulating air pressure within the intake manifold 30 and the intake port 22. In addition, a flow regulating device, such as a gas valve 34, may be positioned between a gas rail 36 at an upstream side and the intake port 22 at a downstream side. A nozzle portion of the valve 34 may extend into the intake port 22 and deliver gaseous fuel thereto for mixing with air from the intake manifold 30 prior to the delivery of the air/gaseous fuel mixture to the cylinder 18. The gas rail 36 may be supplied with gaseous fuel from a gaseous fuel source 38 by a fuel path 40, and a solenoid operated gaseous fuel shut-off valve 42 may be positioned along the fuel path 40. The gaseous fuel source 38 may provide a natural gas fuel that may contain various combustible constituents such as, but not limited to, methane, ethane, propane, butane, nitrogen, and/or carbon dioxide in various relative percentages, although other types of gaseous fuel may be provided as well.

The engine 12 may further include a flow regulating device for the secondary fuel, such as a fuel injector 44, that may inject the secondary fuel such as diesel fuel into the combustion chamber 16. The secondary fuel may be provided to the fuel injector 44 from a common rail 46 that is supplied with fuel from a fuel source 48 via a fuel path 50. A solenoid operated shut-off valve 52 may be positioned along the fuel path 50 to cut off the flow of secondary fuel if necessary. Although the engine 12 is shown in FIG. 1 with a single cylinder 18, the engine may include a plurality of cylinders 18 wherein a single gas rail 36 and a single common rail 46 supply each of the cylinders 18 with the gaseous fuel and the secondary fuel, and wherein a separate intake port 22, gas valve 34, and fuel injector 44 is associated with each one of the cylinders 18. If the engine 12 has a plurality of cylinders 18, the engine 12 may be of the in-line type, V-type, or rotary type.

The engine 12 may operate in 'dual fuel mode' in which the both the gaseous fuel and the diesel fuel (or other secondary fuel) may be supplied to the cylinder(s) 18 in various relative percentages via the gas valve 34 and the fuel injector 44, respectively. Alternatively, the engine 12 may operate in 'diesel mode' in which the gas valve 34 may be closed while pressurized liquid fuel is injected into the cylinder 18 by the fuel injector 44 as the only source of energy during combustion. In addition, the engine 12 may operate in 'gas mode' in which the gaseous fuel is the primary fuel source and the diesel fuel (or other secondary fuel) is used only as an ignition source. In 'gas mode', the gaseous fuel from the gaseous fuel source 38 may be discharged into the intake port 22 by the gas valve 34 and may be mixed with air from the air intake manifold 30, while a small amount or pilot amount of the diesel fuel may be injected into the cylinder 18 by the fuel injector 44 in order to ignite the mixture of the air and the gaseous fuel in the combustion chamber 16. Alternate implementations of the system 10 may allow the engine 12 to be powered by additional fuels that may be available. In such implementations, additional fuel control valves/injectors, rails, fuel sources, and shut-off valves may be provided to control the flow of the additional fuels.

The electronic control module (ECM) 14 of the engine system 10 may be in electronic communication with various components of the engine 12 and may control the apportionment of the fuel sources to the engine to provide the required power to the engine 12. It may also perform estimates of the specific gravity (SG) and lower heating value (LHV) of the gaseous fuel source, as will be described in further detail below. The ECM 14 may include a microprocessor or processor 54 for executing specified programs that control and monitor various functions associated with the system 10. The microprocessor 54 may include a memory 56, such as a read only memory (ROM) 58 that may store a program or several programs, as well as a random access memory (RAM) 60 that may serve as a working memory area for use in executing the program(s) stored in the memory 56. Although the microprocessor 54 is shown, it is also possible to use other electronic components such as a microcontroller, an ASIC (application specific integrated circuit) chip, or any other integrated circuit device.

In order to monitor the performance of the engine 12 and to perform other functions, the ECM 14 may be in electronic communication with a pressure sensor 62 in the gas rail 36, an intake air pressure sensor 64 in the intake manifold 30, and a pressure sensor 66 in the common rail 46 via conductive paths capable of transmitting pressure indicative signals to the ECM 14. In addition, the ECM 14 may be in electronic connection with temperature sensors 68 and 70 provided in the gas rail 36 and the common rail 46, respectively, via conductive paths capable of transmitting temperature indicative signals to the ECM 14. The ECM 14 may also be in electronic communication with and may control each of the gas valve 34, the fuel injector 44, and the airflow controller 32 via conductive pathways. In this regard, the ECM 14 may be electrically connected to and may regulate various actuators for the fluid flow regulating devices of the engine 12, such as the gas valve 34, the fuel injector 44, and the airflow controller 32. The ECM 14 may include driver circuitry or software for delivering current control signals to the gas valve 34, the fuel injector 44, and the airflow controller 32 to control the flow rates/pressures of the corresponding fuel or air. However, it will also be understood that such driver circuitry could be implemented separate from, but connected to, the ECM 14.

Furthermore, the ECM 14 may also be in electronic communication with an engine speed sensor 72 which may be associated with a camshaft or other component of the engine 12, as well as an indicated mean effective pressure (IMEP) sensor 74 which may be positioned within the cylinder 18. The IMEP sensor 74 may detect the IMEP of the engine 12 and may transmit signals representative of the engine's IMEP to the ECM 14. The IMEP may be determined from the in-cylinder pressure over the engine's combustion cycle, and may provide a measure of the energy released or work performed in the cylinder 18 over the engine's combustion cycle.

Figure 2:
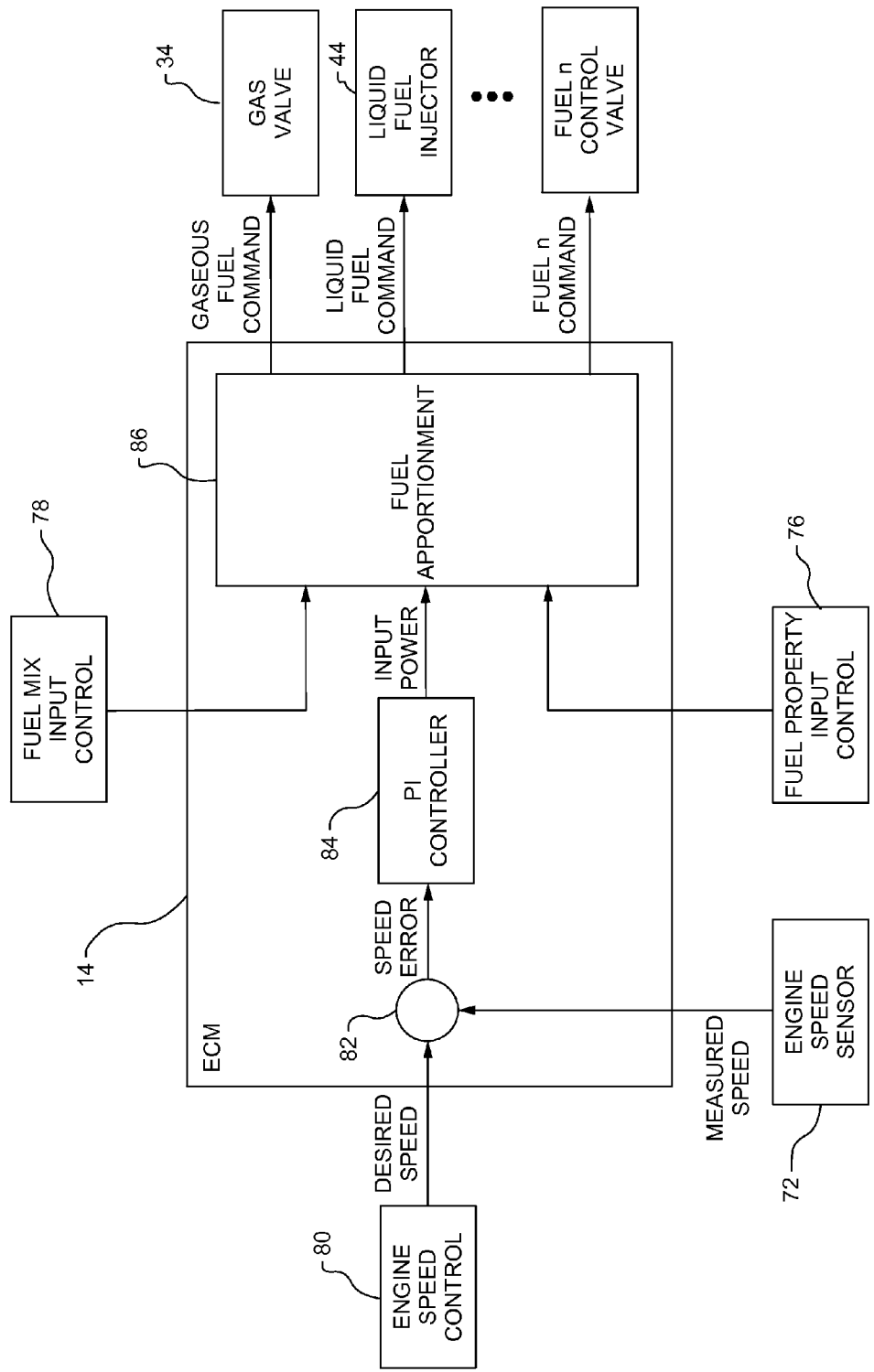
FIG. 2 is a schematic block diagram of a fuel apportionment control strategy implemented by an electronic control module (ECM) of the engine system of FIG. 1, in accordance with the present disclosure.

Referring now to FIG. 2, the ECM 14 may be used to implement a fuel apportionment strategy which may apportion fuels to the engine 12 according to the power needs of the engine 12 as well as fuel property data and fuel mix data provided at a fuel property input control 76 and a fuel mix input control 78. The fuel property input control 76 may be any appropriate input device (e.g., a computer terminal, remote computing device, external storage device connected to the ECM 14, etc.) allowing an operator, technician, or other user of the engine system 10 to input information regarding the properties of the fuels available for use by the system 10. Examples of fuel property data include the density or specific gravity (SG) for a fuel, and a lower heating value (LHV) for a fuel which indicates an amount of energy released by the fuel per unit of mass or volume. Although well understood by those skilled in the art, an LHV for a fuel may be understood as the enthalpy of all combustion products, minus the enthalpy of the fuel at a reference temperature, minus the heat of vaporization of the vapor content of the combustion products.

The fuel mix input control 78 may be any appropriate input device (e.g., a computer terminal, remote computing device, external storage device connected to the ECM 14) allowing an operator, technician, or other user of the multi-fuel engine system 10 to input information regarding the apportionment of the fuels available for use by the system 10. The fuel mix data input at the fuel mix input control 78 may specify the fuel substitution ratios (FSR), or fractions for usage of each of the available fuels, for meeting the input power necessary to operate the engine 12 at the engine speed specified at an engine speed control 80. The engine speed control 80 may be any type of input device (e.g., a gas pedal of a vehicle or excavating machine, a thrust lever of an airplane, etc.) allowing an operator to specify a desired speed at which the engine 12 should operate to perform a desired task. For example, when the engine 12 is operating in dual fuel mode with natural gas and diesel fuel, it may be desired to have the natural gas provide 80% of the power requirement and the diesel fuel provide the remaining 20% of the power requirement, in which case a fuel substitution ratio of 0.80 for the natural gas may be input at the fuel mix input control 78. Where more fuels are available, a fuel substation ratio or fraction may be input for each available fuels in this way. To ensure that 100% of the input power requirement is provided by the fuels, the fuel mix input control 78 may be configured to restrict entry of the fuel substitution ratios of each of the available fuels, $FSR_i$, to those satisfying the equation:

$$\Sigma_{i=1}^{n} FSR_i = 1 \quad (1)$$

The fuel apportionment strategy may begin with an adder 82 of the ECM 14 that may compare a desired speed of the engine 12 input at the engine speed control 80 to a current measured speed of the engine 12 provided by the engine speed sensor 72. The adder 82 may subtract the measured speed of the engine 12 from the desired speed to arrive at a speed error. The speed error may occur due to a change in the commanded speed at the engine speed control 80, or due to a change in the actual speed of the engine 12 caused by an event such as a change in the load or torque of the engine 12. The speed error may be transmitted from the adder 82 to a proportional-integral (PI) controller 84 of the ECM 14. The PI controller 84 may be configured to use the speed error to determine an input power to be provided by the available fuels to cause the actual or measured engine speed to increase or decrease toward the desired engine speed.

A fuel apportionment module 86 of the ECM 14 may use the input power determined by the PI controller 84, along with data provided by the fuel property input control 76 and the fuel mix input control 78, to apportion the power demand between the available fuels. It is noted that prior to the fuel apportionment by the fuel apportionment module 86, the ECM 14 may assume that the engine 12 is operating solely on the secondary fuel source (e.g., diesel fuel). When the input power is transmitted to the fuel apportionment module 86 from the PI controller 84, the fuel apportionment module 86 may retrieve the fuel property and fuel mix data from the fuel property input control 76 and the fuel mix input control 78. The fuel apportionment module 86 may then use the fuel property and fuel mix data to determine a mass flow ($m_i$) for each fuel based on the following equation:

$$\dot{m}_i = \frac{FRS_i \times \text{Input Power}}{LHV_i} \quad (2)$$

where $FSR_i$ is the unitless FSR for the $i^{th}$ fuel, input power is the commanded power transmitted from the PI controller 84 having the units of energy per unit time, and $LHV_i$ is the lower heating value for the $i^{th}$ fuel having units of energy per unit mass. Thus, equation (2) yields $m_i$ in units of mass per unit time for each of the available fuels to provide the commanded power to the engine 12. After determining the mass flow for each of the available fuels, the fuel apportionment module 86 may format commands for the actuators of the fluid flow regulating devices (the gas valve 34, the fuel injector 44, etc.) to cause the devices to provide the required mass flow ($m_i$) to the engine 12. In particular, the fuel apportionment module 86 may transmit a separate control signal to each of the fuel flow regulating devices to regulate the fuel mass flow through each. It is noted that the operation of the fuel apportionment strategy disclosed herein is also described in U.S. application Ser. No. 13/919,166.

Figure 3:
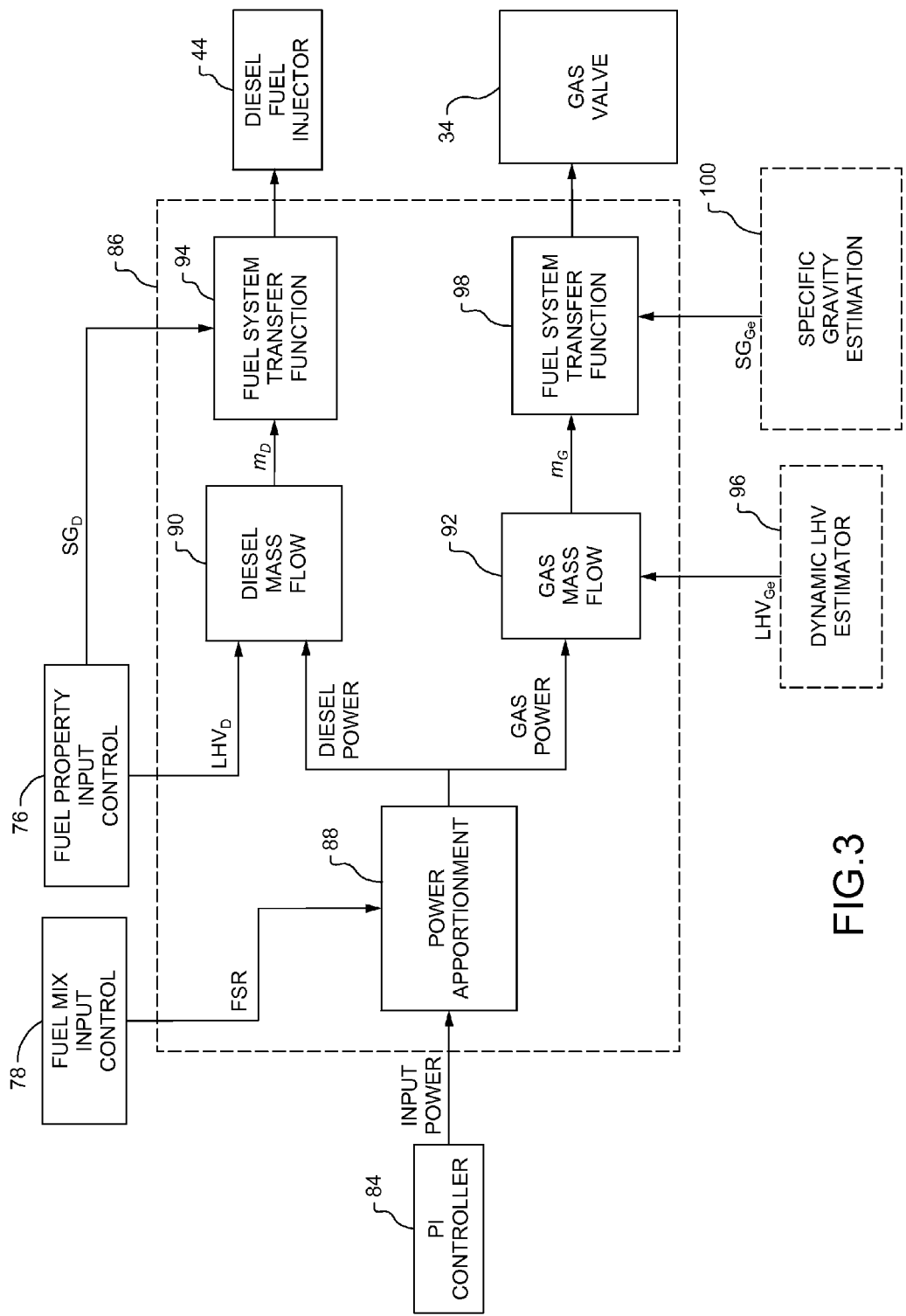
FIG. 3 is a schematic block diagram of an exemplary fuel apportionment module capable of implementing some of the functions of the fuel apportionment strategy of FIG. 2, in accordance with the present disclosure.

Further details of the fuel apportionment strategy as applied in a dual fuel engine powered by a gaseous fuel having an unknown composition (e.g., natural gas) and diesel fuel is shown in FIG. 3. The fuel apportionment module 86 may include a power apportionment module 88 that may receive the input power command from the PI controller 84 and the diesel/gaseous fuel FSR from the fuel mix input control 78. The power apportionment module 88 may then determine the amount of power to be provided by the diesel fuel (in units of energy per unit time) by multiplying the FSR for the diesel fuel by the input power, and may output a diesel power command to a diesel mass flow module 90. In addition, the power apportionment module 88 may also determine the amount of power to be provided by the gaseous fuel (in units of energy per unit time) by multiplying the FSR for the gaseous fuel by the input power requirement, and may output a gas power command to a gas mass flow module 92. The diesel mass flow module 90 may determine the diesel mass flow ($m_D$) based on the diesel power command and the lower heating value for the diesel fuel, $LHV_D$, as obtained from the fuel property input control 76, by dividing the diesel power command by $LHV_D$. In addition, the diesel mass flow module 90 may output a diesel mass flow, $m_D$, request to a diesel fuel system transfer function 94 which may control the fuel injector 44 for diesel to provide the requested diesel mass flow. Specifically, the fuel system transfer function 94 may control the diesel injection duration according to the requested diesel mass flow as well as the properties of the diesel fuel provided by the fuel property input control 76, such as the known specific gravity of the diesel fuel ($SG_D$).

As the exact composition of the gaseous fuel may be unknown or changing with time, the specific gravity and the lower heating value for the gaseous fuel may also be unknown. Thus, the gas flow module 92 may estimate the gas mass flow ($m_G$) using an estimated lower heating value for the natural gas ($LHV_{Ge}$) provided by a dynamic LHV estimation module 96 of the ECM 14 as will be described in further detail below. A gas fuel system transfer function 98 may receive a gas mass flow ($m_G$) request from the gas mass flow module 92 and may regulate the gas valve 34 accordingly to provide the requested gas mass flow. Specifically, the gas fuel system transfer function 98 may control the open duration of the gas valve 34 based on the gas mass flow request ($m_G$) as well as the estimated specific gravity of the gaseous fuel ($SG_{Ge}$) provided by a specific gravity estimation module 100 of the ECM 14 as will be described in further detail below. For example, if the gaseous fuel has a relatively low estimated specific gravity ($SG_{Ge}$), the fuel system transfer function 98 may specify longer open durations of the gas valve 34 to provide the requested gas mass flow.

Figure 4:
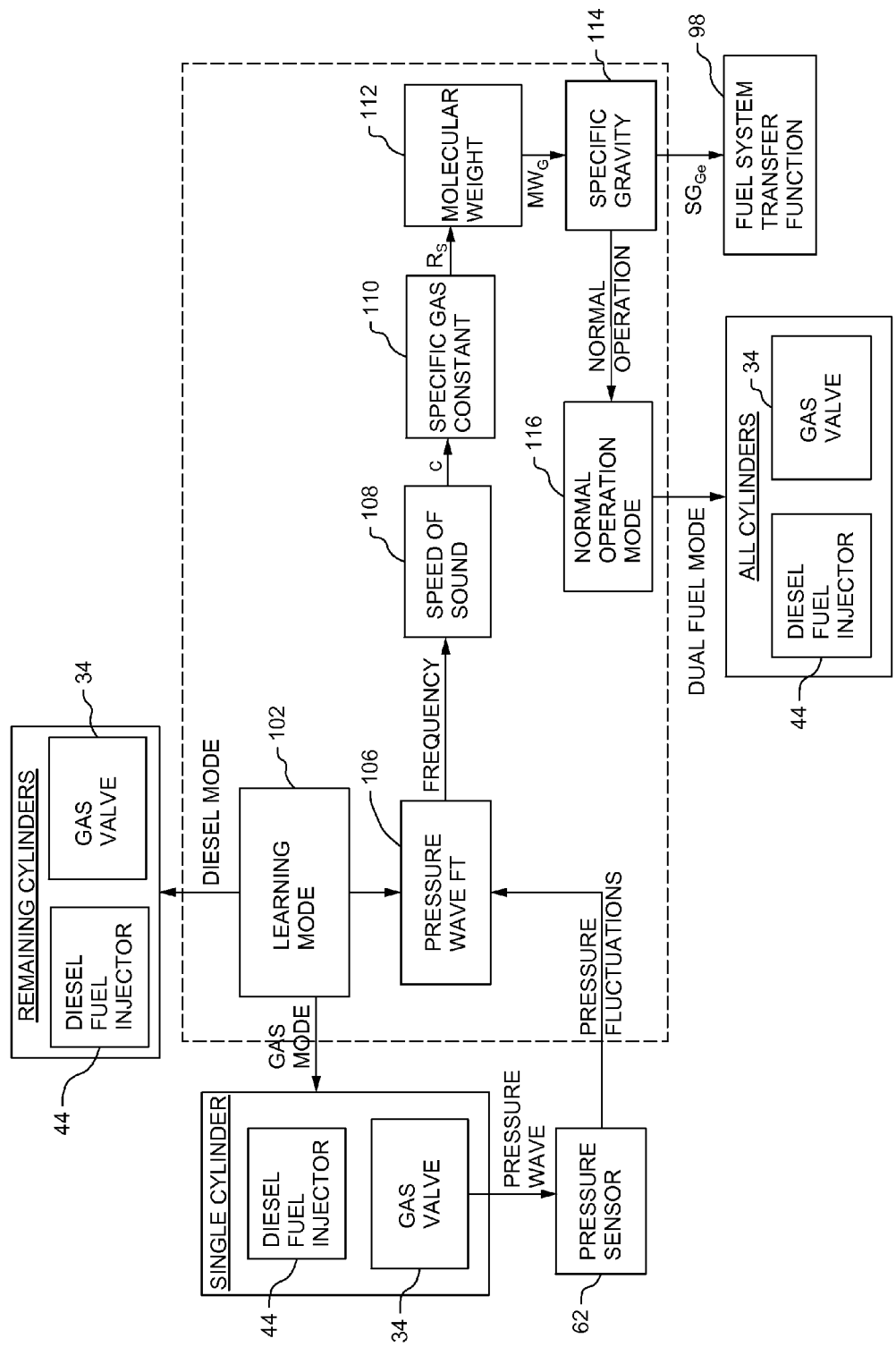
FIG. 4 is a schematic block diagram of an exemplary specific gravity estimation module of the ECM, in accordance with the present disclosure.

The specific gravity estimation module 100 is shown in FIG. 4. The specific gravity estimation module 100 may include a learning mode module 102 which may shift the engine 12 to a 'learning mode' during which the properties of the natural gas, or other gaseous fuel, are studied by the module 100. Specifically, if the engine 12 includes a plurality of cylinders 18, then the learning mode module 102 may send a 'gas mode' command to one of the cylinders 18 to cause the cylinder 18 to operate in 'gas mode' in which the gaseous fuel is the primary fuel source and the diesel fuel is used only as an ignition source for the gaseous fuel. In addition, the learning mode module 102 may send a 'diesel mode' command to the remaining cylinders 18 to cause the remaining cylinders 18 to operate in 'diesel mode' in which only diesel fuel is combusted in the cylinders 18. Specifically, the 'diesel mode' command may trigger the closing of the gas valves 34 of the remaining cylinders 18. If the engine 12 is a V-engine with the cylinders 18 arranged in a "V", one cylinder 18 from each bank may run in 'gas mode' and the remaining cylinders 18 in each bank may run in 'diesel mode'. If the engine 12 is of the in-line type, then one of the cylinders 18 in a row of the cylinders 18 may run in 'gas mode' and the remaining cylinders 18 may run in 'diesel mode'. If, however, the engine 12 has just one cylinder 18, then the learning mode module 102 may send the 'gas mode' command to the cylinder 18 to cause the cylinder 18 to operate in 'gas mode'.

Running one of the cylinders 18 in 'gas mode' may enable the pressure dynamics in the gas rail 36 caused by the opening and closing of the gas valve 34 associated with the cylinder 18 operating in 'gas mode' to be clearly detected without interference from the opening and closing of the other gas valves of the engine 12. The opening and closing of the gas valve 34 of the cylinder 18 running in 'gas mode' may produce a reflected pressure wave in the gas rail 36 that may be detected by the pressure sensor 62. The pressure wave in the gas rail 36 may reflect off the ends 104 of the gas rail 36 and may travel at the speed of sound (c) in the natural gas. The back and forth reflection of the pressure wave in the gas rail 36 may be detected as local fluctuations in pressure at the pressure sensor 62. The pressure sensor 62 may transmit the pressure fluctuation signals to a pressure wave Fourier transform (FT) module 106 of the specific gravity estimation module 100 which may then determine the frequency of the back and forth reflection of the pressure wave in the gas rail 36 by Fourier transform.

The pressure wave FT module 106 may transmit the frequency of the pressure wave to a speed of sound module 108 that may determine the speed of sound (c) in the gaseous fuel based on the frequency of the pressure wave. As the the peak to peak time of the pressure wave frequency may correlate with the time it takes for the pressure wave/sound wave to travel back and forth once from the pressure sensor 62 to one of the ends 104 of the gas rail 36, the speed of sound module 108 may calculate the speed of sound (c) in the gaseous fuel based on the peak to peak time of the pressure wave frequency and the known distance between the pressure sensor 62 and the end 104 of the gas rail 36.

Once calculated, the speed of sound module 108 may output the speed of sound (c) in the gaseous fuel to a specific gas constant module 110 which may estimate the specific gas constant ($R_s$) of the gaseous fuel by solving the following equation for $R_s$:

$$c = \mathrm{sqrt}(kR_sT) \qquad (3)$$

where c is the speed of sound in the gaseous fuel, k is the ratio of specific heats of the gaseous fuel (or the ratio of the specific heat at constant pressure ($C_p$) to the specific heat at constant volume ($C_v$)), $R_s$ is the specific gas constant of the gaseous fuel, and T is temperature. The values for c and T may be known, whereas the value for k may be an estimated default value that is pre-programmed into the specific gas constant module 110. As the value for k may be an estimate, the specific gas constant, $R_s$, determined by the specific gas constant module 110 may be an estimated value as well.

The specific gas constant module 110 may output the estimated $R_s$ to a molecular weight module 112 which may estimate the molecular weight of the gaseous fuel ($MW_G$) using the following equation:

$$MW_G = R/R_s \qquad (4)$$

where R is the ideal gas constant and $R_s$ is the specific gas constant input to the specific gas constant module 110. Again, the $MW_G$ determined by the molecular weight module 112 may be an estimate as it is dependent upon an estimated value for k. The molecular weight module 112 may output the $MW_G$ value to a specific gravity module 114 which may estimate the specific gravity of the gaseous fuel using the following equation:

$$SG_{Ge} = MW_G/MW_{air} \qquad (5)$$

where $SG_{Ge}$ is the estimated specific gravity of the gaseous fuel and $MW_{air}$ is the known molecular weight of air.

The specific gravity estimation module 100 may then output the estimated specific gravity ($SG_{Ge}$) to the gas fuel system transfer function 98 so that the fuel system transfer function 98 may regulate the open duration of the gas valve 34 to provide a gas flow that more accurately reflects the requested gas mass flow, $m_G$. For example, a higher $SG_{Ge}$ value for the gaseous fuel may lead to shorter open durations of the gas valve 34, whereas a lower $SG_{Ge}$ value for the gaseous fuel may lead to longer open durations of the gas valve 34. Once the $SG_{Ge}$ estimation is complete, the specific gravity module 114 may send a 'normal operation' request to a normal operation mode module 116 to notify the module 116 that the 'learning mode' is complete and that the normal operation of the engine 12 may resume. The normal operation mode module 116 may then send a 'dual fuel mode' request to all of the cylinders 18 of the engine to cause the cylinders 18 to operate in 'dual fuel mode' in which both the gaseous fuel and the diesel fuel are supplied to the cylinders 18 for combustion. In particular, the 'dual fuel mode' request may trigger the opening of the gas valves 34 for the cylinders 18 running in 'diesel mode'. It will be understood that, in some arrangements, the 'dual fuel mode' may include the 'gas mode' in which the gaseous fuel is the primary fuel source and the diesel fuel is only used for ignition of the gaseous fuel in the cylinders 18. The 'learning mode' and the estimation of the specific gravity of the gaseous fuel by the specific gravity estimation module 100 may be implemented at the initial start of the engine 12, when the gaseous fuel source is changed, and/or periodically during engine operation in situations in which it is expected that the composition and properties of the gaseous fuel are changing with time.

Figure 5:
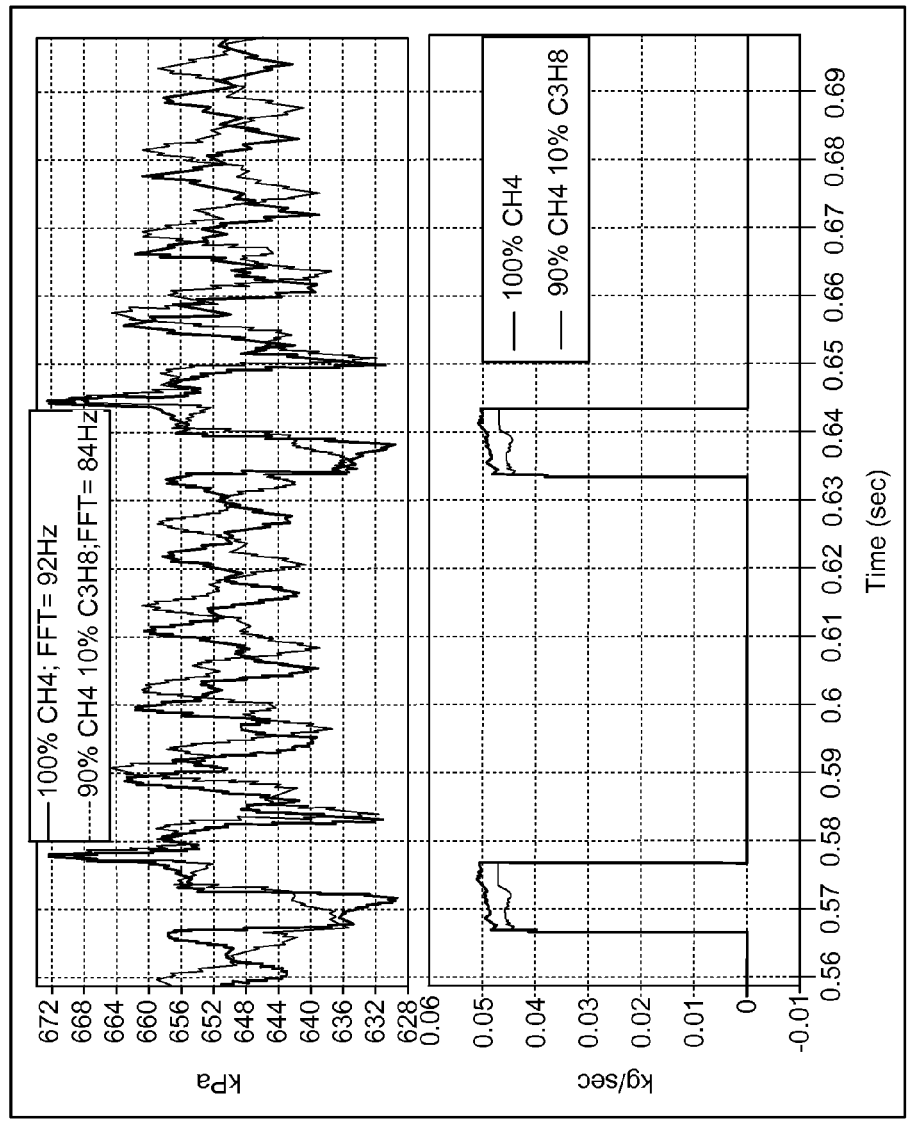
FIG. 5 is a 1D simulation of pressure waves in a gas rail of the engine generated by the opening and closing of a gas valve for two different gaseous fuel compositions (top), and a corresponding plot of the gaseous fuel flow rate through the gas valve (bottom), in accordance with the present disclosure.

FIG. 5 shows a 1D simulation of pressure waves generated in a model gas rail by the opening and closing of a gas valve for two different gaseous fuel compositions (top), and the corresponding gas mass flow rates through the gas valve during two separate injection events for the two different gaseous fuel compositions (bottom). As can be seen, each injection event produces corresponding ringing in the gas rail caused by the reflected pressure wave. It can also be seen that the two different gaseous fuel compositions produce distinct pressure wave traces, supporting that the pressure wave dynamics in the gas rail may be used to derive the physical properties of various unknown gaseous fuel sources.

Figure 6:
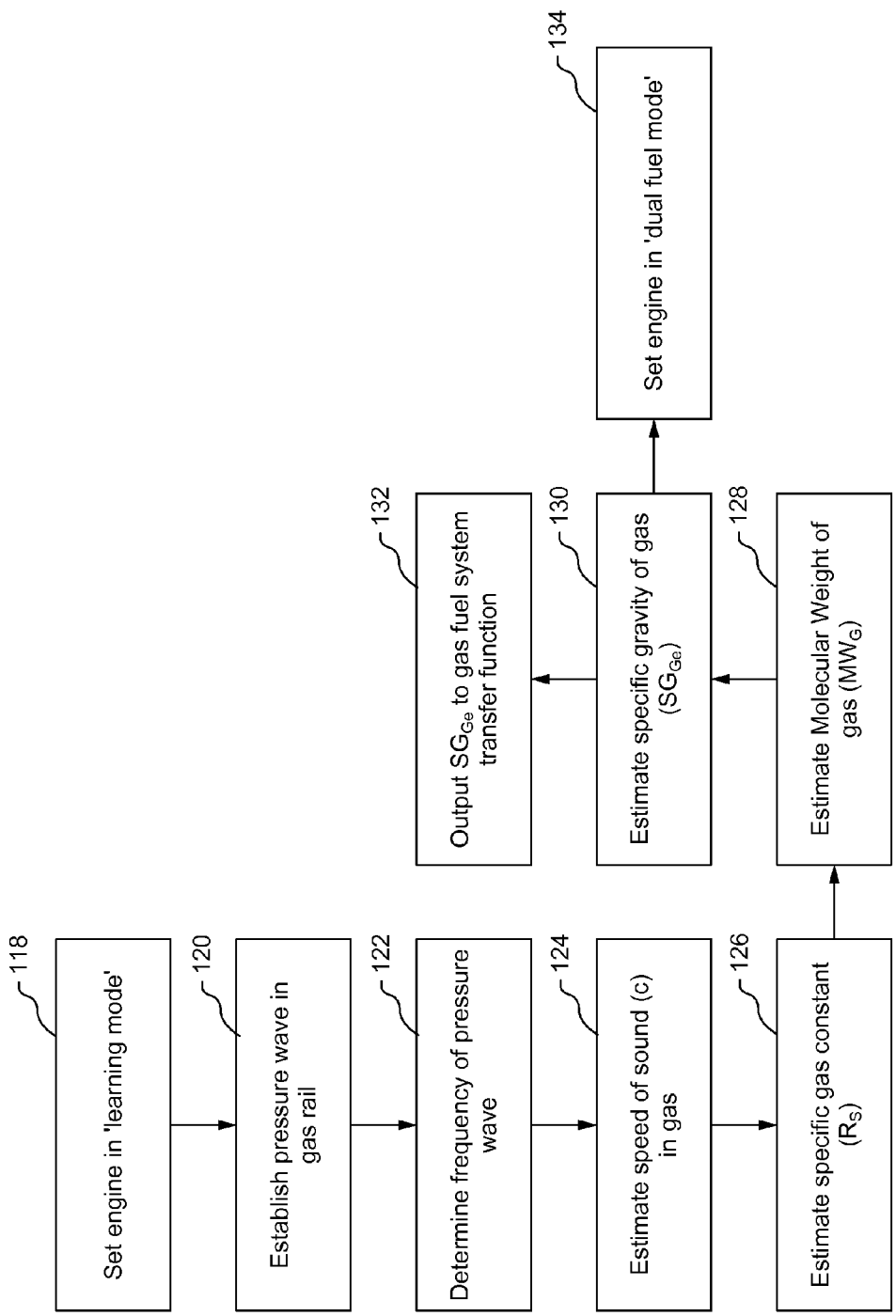
FIG. 6 is a flowchart of an exemplary method for estimating the specific gravity of the gaseous fuel as implemented by the specific gravity estimation module of FIG. 4, in accordance with a method of the present disclosure.

Turning now to FIG. 6, a method for estimating a specific gravity of an unknown gaseous fuel that powers the engine 12 is shown. The method of FIG. 6 may be implemented by the specific gravity estimation module 100 of FIG. 4. Starting with a first block 118, the engine 12 may be set in 'learning mode' to allow the properties of the gaseous fuel to be studied. Namely, the block 118 may involve setting one of the cylinders 18 in 'gas mode' and the remaining cylinders in 'dual fuel mode' to allow clear detection of the pressure dynamics in the gas rail 36 caused by the opening and closing of a single gas valve 34. According to a next block 120, the pressure wave may be established in the gas rail 36 by the opening and closing of the gas valve 34 associated with the cylinder 18 operating in 'gas mode'. According to the following blocks 122 and 124, the frequency of the pressure wave in the gas rail 36 may be determined by Fourier transform (block 122), and the speed of sound (c) in the gaseous fuel may be calculated (block 124). The block 124 may involve correlating the peak to peak time of the pressure wave frequency with the speed of sound (c) in the gaseous fuel using the known geometry of the gas rail 36 as explained above.

According to a next block 126, the specific gas constant ($R_s$) may be estimated by based on the speed of sound (c) in the gaseous fuel by solving equation (3) for $R_s$ using a default value or an estimated value for k. The molecular weight of the gaseous fuel ($MW_G$) may then be estimated based on the estimated value for $R_s$ according to equation (4) (block 128), and the specific gravity of the gaseous fuel may be estimated based on $MW_G$ according to equation (5) (block 130). With an estimated value of the specific gravity ($SG_{Ge}$) of the gaseous fuel at hand, the $SG_{Ge}$ value may then be output to the gas fuel system transfer function 98 (block 132) to allow the fuel system transfer function 98 to provide a more accurate gas mass flow, $m_G$. As will be understood, the air/fuel ratio of the engine 12 may also be more accurately regulated with the gas mass flow accurately controlled. With the improved ability to accurately regulate the gas mass flow, the engine may then be set in 'dual fuel mode' according to a block 134. Specifically, the gas valves 34 of the cylinders 18 that were operating in 'diesel mode' during the 'learning mode' may be re-opened to allow a mixture of the gaseous fuel and the diesel fuel to be supplied to the cylinders 18.

Figure 7:
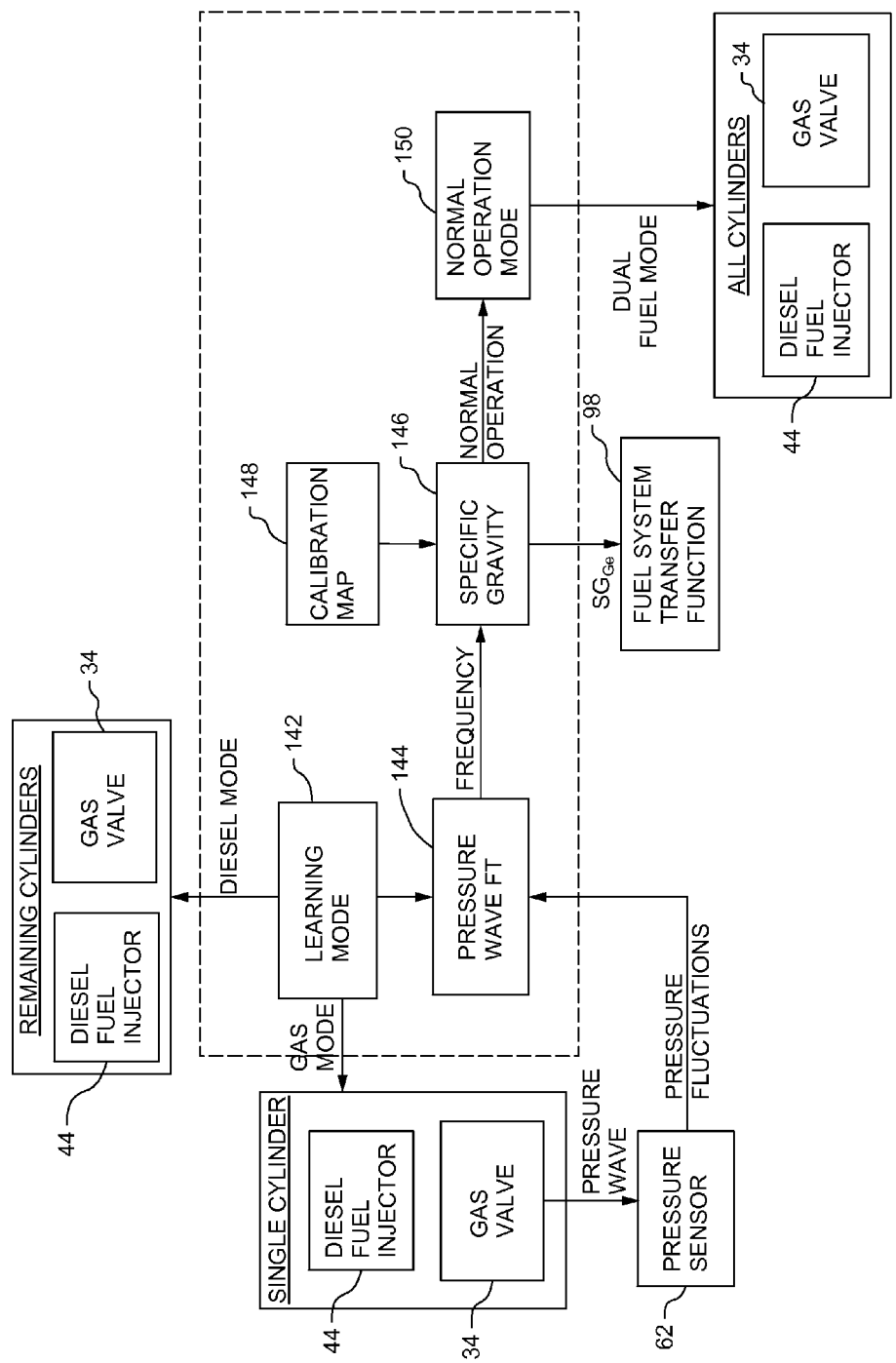
FIG. 7 is a schematic block diagram of another exemplary specific gravity estimation module of the ECM, in accordance with another aspect of the present disclosure.

An alternative specific gravity estimation module 140 of the ECM 14 is shown in FIG. 7. The specific gravity estimation module 140 may have a learning mode module 142 that may shift the engine 12 to 'learning mode' in which one of the cylinders 18 of the engine operates in 'gas mode' and the remaining cylinders 18 operate in 'diesel mode' as described in detail above. The opening and closing of the gas valve 34 associated with the cylinder 18 operating in 'gas mode' may then generate a pressure wave in the gas rail 36 which may be detected by the pressure sensor 62. The pressure fluctuation signals detected by the pressure sensor 62 may be transmitted to a pressure wave FT module 144 of the specific gravity estimation module 140. The pressure wave FT module 144 may use Fourier transform to determine the frequency of the pressure wave in the gas rail 36, and may output the pressure wave frequency to a specific gravity module 146, as shown. The specific gravity module 146 may determine the specific gravity of the gaseous fuel by comparing the measured pressure wave frequency with a calibration map 148 that correlates gaseous fuel pressure wave frequencies with gaseous fuel specific gravities. The calibration map 148 may be prepared by experimentally measuring the pressure wave frequencies in the gas rail 36 caused by the opening and closing of the gas valve 34 carrying known gaseous fuel samples with known specific gravities.

Once the specific gravity module 146 has determined the specific gravity of the gaseous fuel, it may output the specific gravity ($SG_{Ge}$) to the gas fuel system transfer function 98 to allow the fuel system transfer function 98 to more accurately control the gas mass flow rate, $m_G$. In addition, the specific gravity module 146 may send a 'normal operation' request to a normal operation mode module 150 to notify the module 150 that the 'learning mode' is complete and that the normal operation of the engine 12 may resume. The normal operation mode module 150 may then transmit a 'dual fuel mode' request to all of the cylinders 18 of the engine 12 which may trigger the re-opening of the gas valves 34 for the cylinders 18 running in 'diesel mode'. As explained above, the 'learning mode' and the estimation of the specific gravity of the gaseous fuel by the specific gravity estimation module 140 may be implemented at the initial start of the engine 12, when the gaseous fuel source is changed, and/or periodically during engine operation in situations in which it is expected that the composition and properties of the gaseous fuel are changing with time.

Figure 8:
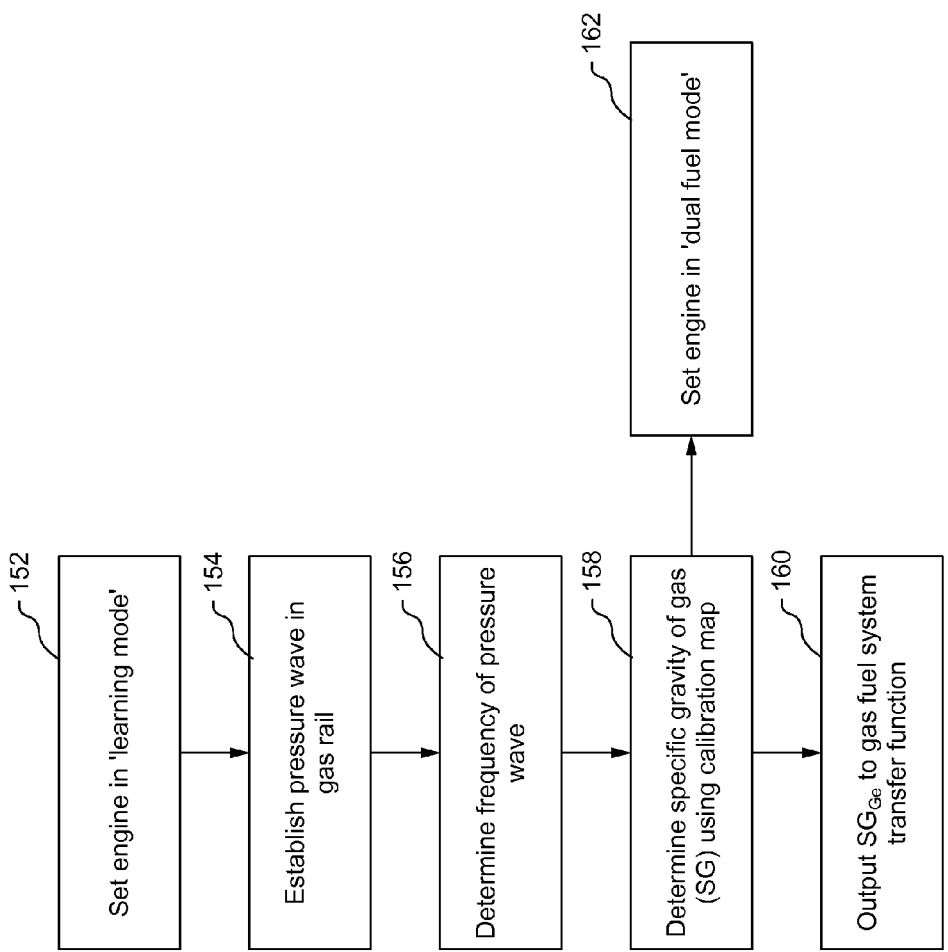
FIG. 8 is a flowchart of an exemplary method for estimating the specific gravity of the gaseous fuel as implemented by the specific gravity estimation module of FIG. 7, in accordance with another method of the present disclosure.

A method of estimating the specific gravity of a gaseous fuel as performed by the specific gravity estimation module 140 is shown in FIG. 8. Beginning with a first block 152, the engine 12 may be set in 'learning mode' in which one of the cylinders is set in 'gas mode' and the remaining cylinders 18 are set in 'diesel mode'. According to a next block 154, a pressure wave in the gas rail 36 may be established by the opening and closing of the gas valve 34 associated with cylinder 18 operating in 'gas mode'. The frequency of the pressure wave may then be determined by Fourier transform (block 156), and the frequency of the pressure wave may be correlated with a specific gravity of the gaseous fuel ($SG_{Ge}$) by comparison with the calibration map 148 (block 158). Once the specific gravity estimation is complete, the $SG_{Ge}$ value may be output to the gas fuel system transfer function 98 (block 160), and the engine 12 may be set in 'dual fuel mode' (block 162) by triggering the re-opening of the gas valves 34 of the cylinders 18 that were operating in 'diesel mode' during the 'learning mode' of the engine 12.

Figure 9:
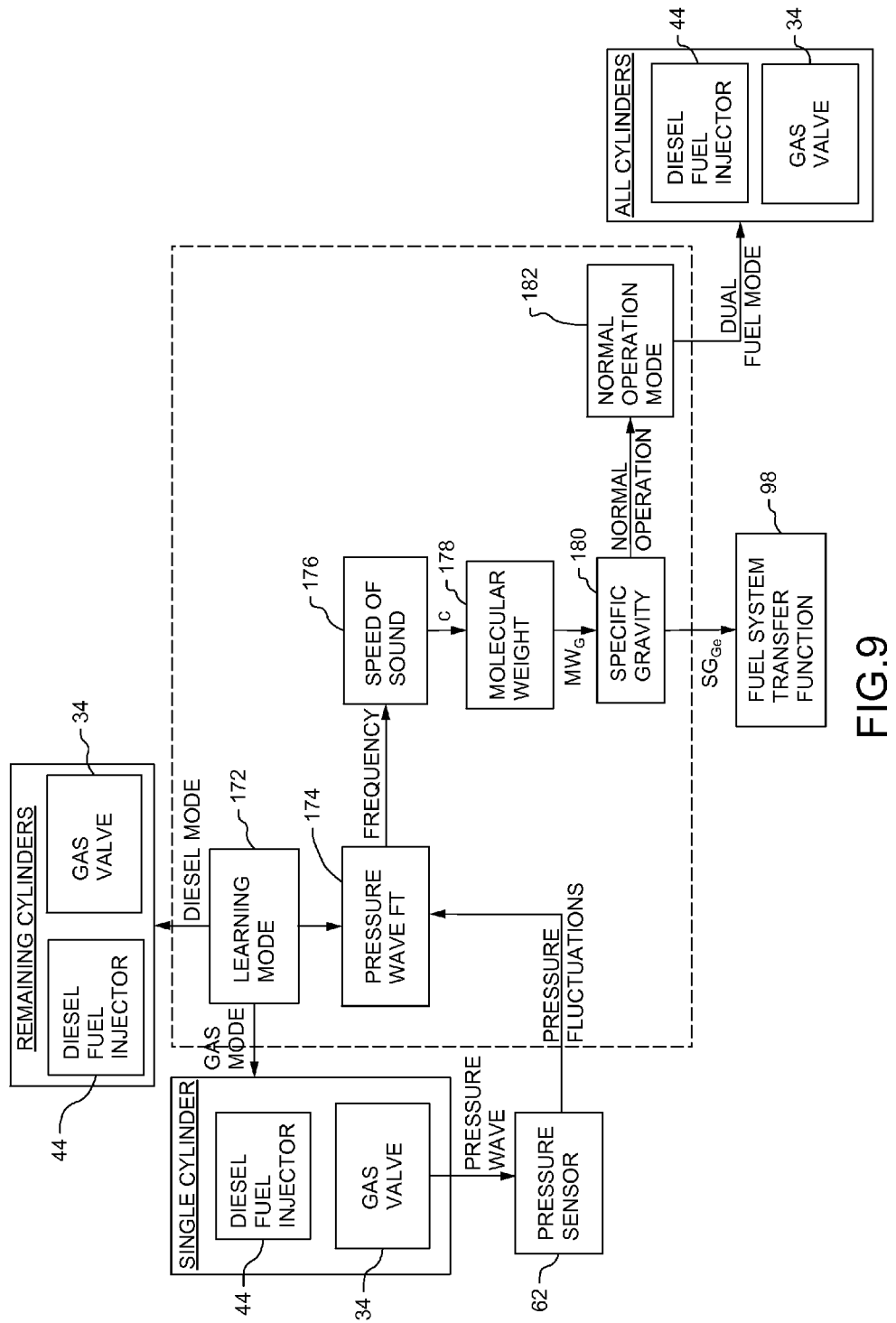
FIG. 9 is a schematic block diagram of another exemplary specific gravity estimation module of the ECM, in accordance with another aspect of the present disclosure.

Another alternative specific gravity estimation module 170 of the ECM 14 is shown in FIG. 9. Like the specific gravity estimation modules 100 and 140 of FIGS. 4 and 7, the specific gravity estimation module 170 may include a learning mode module 172 that may shift the engine 12 to 'learning mode' in which one of the cylinders 18 of the engine 12 operates in 'gas mode' and the remaining cylinders 18 operate in 'diesel mode'. Once shifted to 'learning mode', the gas valve 34 associated with the cylinder 18 operating in 'gas mode' may generate a pressure wave in the gas rail 36 which may be detected by the pressure sensor 62. The pressure sensor 62 may transmit the pressure fluctuation signals to a pressure wave FT module 174 that may derive the frequency of the pressure wave by Fourier transform. The frequency of the pressure wave may then be transmitted to a speed of sound (c) module 176 which may determine the speed of sound (c) in the gaseous fuel using the peak to peak time of the pressure wave frequency and the known distance between the pressure sensor 62 and the end 104 of the gas rail 36 as explained above.

The speed of sound module 176 may output the calculated speed of sound (c) to a molecular weight module 178 that may calculate the molecular weight of the gaseous fuel ($MW_G$) using a polynomial function relating speed of sound (c) to gaseous fuel molecular weights. The polynomial function used to relate the speed of sound (c) with a gaseous fuel molecular weight may be determined by a data plot of the molecular weight of various ideal gas combinations with the speed of sound (c) of the different ideal gas combinations. In particular, as the value of k and $R_s$ for the ideal gas combinations may be calculated directly by known relations apparent to those skilled in the art, the speed of sound (c) of the ideal gas combinations may be directly calculated according to equation (3) above to provide the polynomial function.

The molecular weight module 178 may then output the $MW_G$ value to a specific gravity module 180 that may calculate the specific gravity ($SG_{Ge}$) of the gaseous fuel according to equation (5) above using the known molecular weight of air ($MW_{air}$). As with the specific gravity estimation modules 100 and 140 described above, the specific gravity module 180 may then output the $SG_{Ge}$ value to the gas fuel system transfer function 98, and may send a 'normal operation' request to a normal operation mode module 182 to notify the module 182 that the 'learning mode' is complete and the normal operation of the engine 12 should resume. In turn, the normal operation mode module 182 may transmit a 'dual fuel mode' request to all of the cylinders 18 to cause all of the cylinders 18 to operate in 'dual fuel mode'. In particular, the 'dual fuel mode' request may trigger the actuators of the gas valves 34 for the cylinders 18 operating in 'diesel mode' to re-open.

Figure 10:
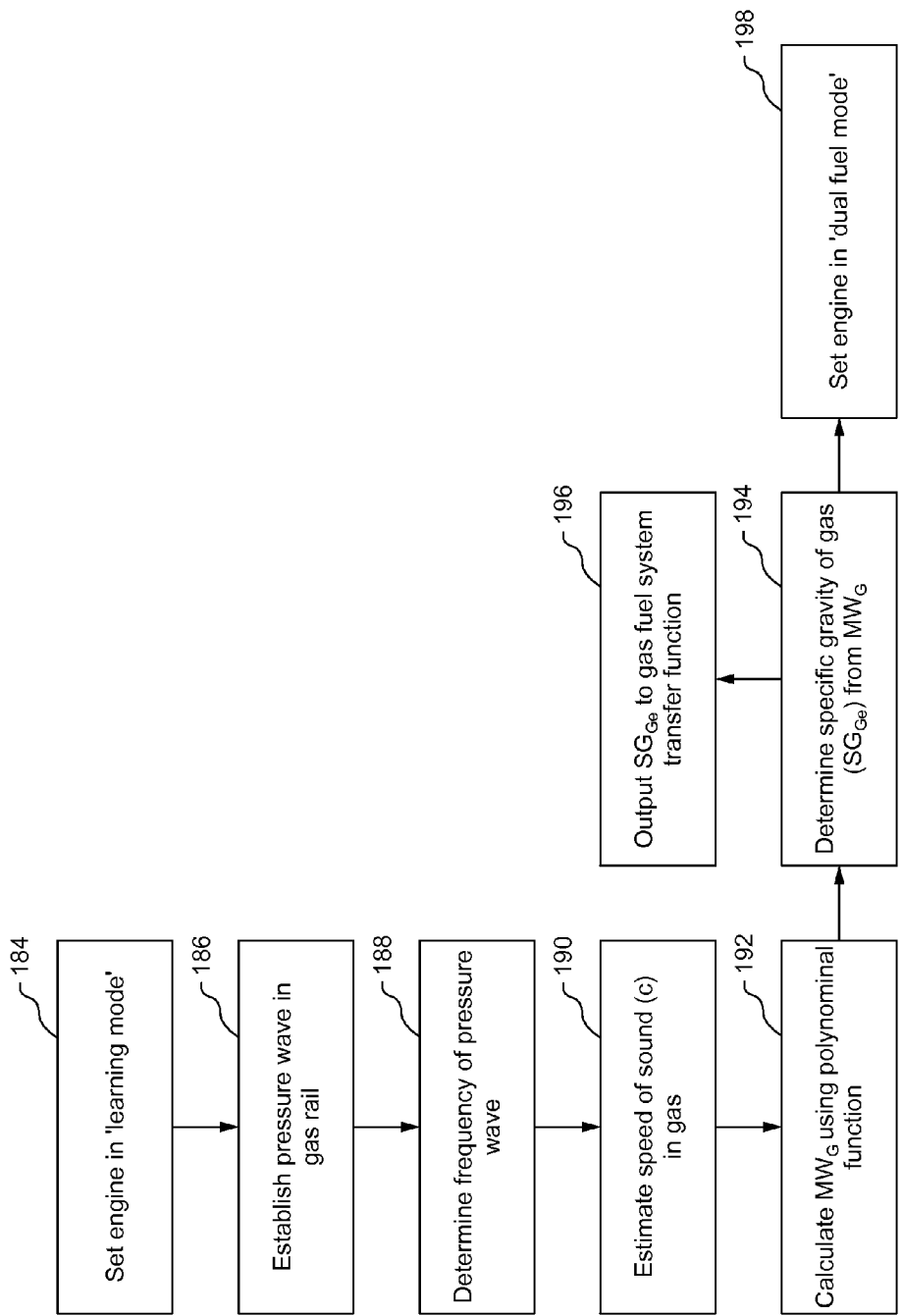
FIG. 10 is a flowchart of an exemplary method for estimating the specific gravity of the gaseous fuel as implemented by the specific gravity estimation module of FIG. 9, in accordance with another method of the present disclosure.

A method of estimating the specific gravity of a gaseous fuel as performed by the specific gravity estimation module 170 is shown in FIG. 10. Beginning with a first block 184, the engine 12 may be set in 'learning mode' by setting one of the cylinders 18 in 'gas mode' and the remaining cylinders 18 in 'diesel mode'. According to a next block 186, a pressure wave may then be established in the gas rail 36 by the opening and closing of the gas valve 34 associated with the cylinder 18 operating in 'gas mode'. The frequency of the pressure wave may then be determined by Fourier transform (block 188), and the frequency of the pressure wave may be correlated with a speed of sound (c) in the gaseous fuel using the peak to peak time of the pressure wave frequency and the known distance between the pressure sensor 62 and the end 104 of the gas rail 36 as described above (block 190). According to a next block 192, the molecular weight of the gaseous fuel ($MW_G$) may be calculated using a polynomial function relating the speed of sound (c) to molecular weight, as described above. The molecular weight of the gaseous fuel ($MW_G$) and the known molecular weight of air ($MW_{air}$) may then be used to calculate the specific gravity of the gaseous fuel using equation (5) above (block 194).

Once the specific gravity of the gaseous fuel is estimated, the $SG_{Ge}$ value may be output to the gas fuel system transfer function 98 (block 196) to allow the fuel system transfer function 98 to more precisely regulate the gas mass flow, $m_G$. In addition, the engine 12 may be reverted to 'dual fuel mode' by causing the gas valves 34 of the cylinders 18 that were operating in 'diesel mode' to re-open (block 198).

Figure 11:
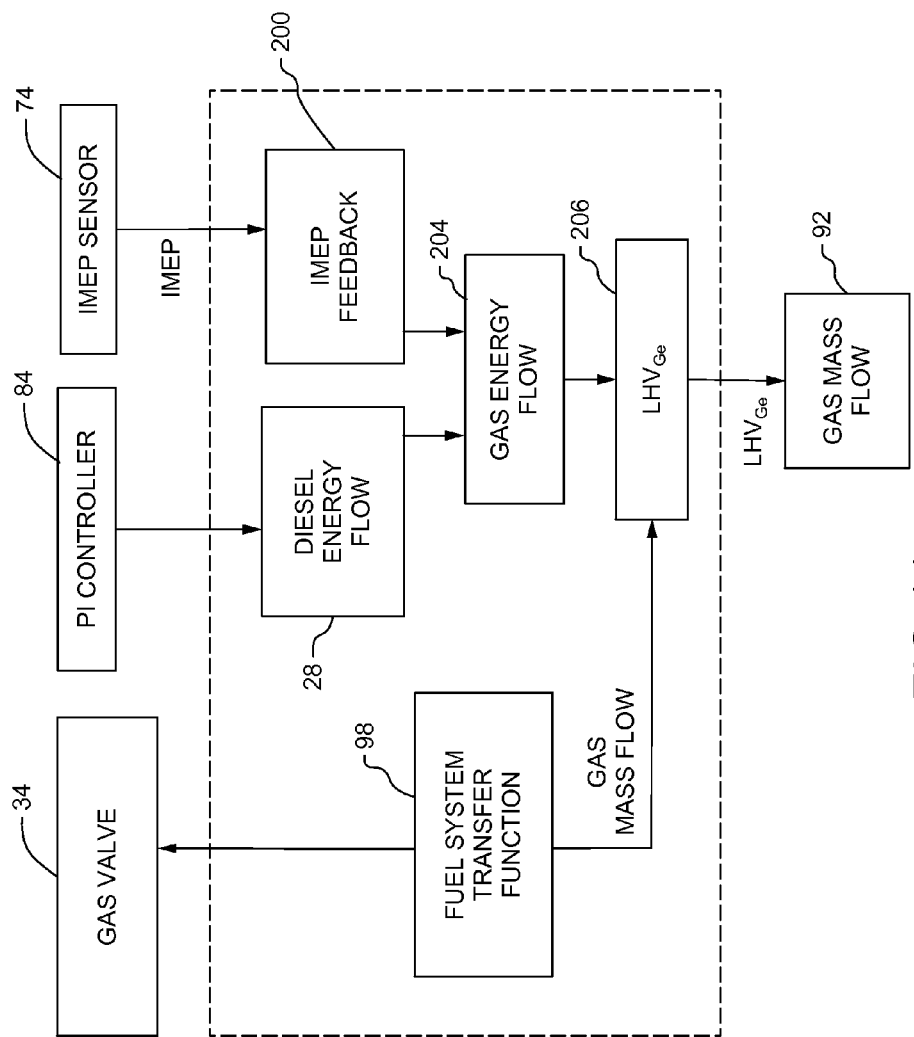
FIG. 11 is a schematic block diagram of a dynamic LHV estimation module of the ECM, in accordance with the present disclosure.

The ability to estimate the specific gravity of the gaseous fuel according to the methods described above may also improve the accuracy of the estimated lower heating value of the gaseous fuel ($LHV_{Ge}$) calculated by the dynamic LHV estimation module 96. In particular, as shown in FIG. 11, the dynamic LHV estimation module 96 may include an IMEP feedback module 200 that may receive the IMEP from the IMEP sensor 74 and may use the IMEP to determine an energy released in the cylinder 18 over the engine's combustion cycle. In addition, the dynamic LHV estimation module 96 may also include a diesel energy flow module 202 that may determine a diesel energy flow based on input from the PI controller 84. As explained above, the PI controller 84 may operate under the assumption that the engine 12 is running on 100% diesel and that all of the input power needed to maintain a speed is provided by the diesel fuel. Thus, the diesel energy flow module 202 may determine the quantity of diesel fuel needed to provide the input power specified by the PI controller 84, and may determine a diesel energy flow in units of energy by multiplying the diesel fuel quantity with the known $LHV_D$ of the diesel fuel.

The dynamic LHV estimation module 96 may also include a gas energy flow module 204 that may receive input of the energy released in the cylinder 18 over the combustion cycle from the IMEP feedback module 200, as well as input of the diesel energy flow from the diesel energy flow module 202. The gas energy flow module 204 may estimate the gas energy flow for the gaseous fuel based on the difference between the energy released in the cylinder 18 and the diesel energy flow. In other words, as the input power may, in actuality, be provided by a combination of the diesel fuel and the gaseous fuel, any difference between the diesel energy flow that assumes the engine 12 is running on pure diesel and the measured energy released in the cylinder by the IMEP sensor 74 may be attributed to the contribution of the gaseous fuel energy to the energy released in the cylinder 18.

An $LHV_{Ge}$ module 206 of the dynamic LHV estimation module 96 may then determine the $LHV_{Ge}$ for the gaseous fuel based on the gas energy flow provided by the gas energy flow module 204 and the gas mass flow, $m_G$, provided by the fuel system transfer function 98. Specifically, the $LHV_{Ge}$ module 206 may determine $LHV_{Ge}$ for the gaseous fuel using the equation:

$$LHV_{Ge} = \text{gas energy flow}/m_G \quad (6)$$

wherein the gas energy flow is provided in units of energy per unit time, and the gas mass flow, $m_G$, is provided in mass per unit time to provide $LHV_{Ge}$ in units of energy per unit mass. The dynamic LHV estimation module 96 may then output $LHV_{Ge}$ to the gas mass flow module 92 as explained above (see FIG. 3). As the accuracy of the $LHV_{Ge}$ determined by the dynamic LHV estimation module 96 is dependent on the accuracy of the gas mass flow, $m_G$, which, in turn, is dependent on the accuracy of the specific gravity value of the gaseous fuel, the ability to estimate the specific gravity of the gaseous fuel using the specific gravity estimation modules 100, 140, or 170 described above may provide more reliable $LHV_{Ge}$ values as well. This may further improve the ability to predict the true amount of gaseous fuel supplied to the cylinder(s) 18 as well as the air/fuel ratio of the engine 12.

INDUSTRIAL APPLICABILITY

The teachings of the present disclosure may find industrial applicability in a variety of settings such as, but not limited to, multi-fuel engines operating with a gaseous fuel source having unknown physical properties, or properties that are changing with time. The technology disclosed herein provides a strategy that allows the dynamic estimation of the specific gravity of an unknown gaseous fuel while the engine is running and while the gaseous fuel is powering the engine. The strategy of the present disclosure involves the generation of a reflected pressure wave in a gas rail of the engine caused by the opening and closing of a gas valve that supplies the gaseous fuel to an intake port of an engine cylinder. Various strategies may then be used to estimate the specific gravity of the gaseous fuel based on the frequency of the pressure wave in the gas rail. In one arrangement, the frequency of the pressure wave may be used to determine the speed of sound in the gaseous fuel, which may then be used to estimate the specific gas constant of the gaseous fuel and, thus, the specific gravity of the gaseous fuel using known relations. In another arrangement, the specific gravity of the gaseous fuel may be estimated by comparing the frequency of the pressure wave in the gas rail with a calibration map that correlates gas rail pressure wave frequencies with gaseous fuel specific gravities. In yet another arrangement, a speed of sound in the gaseous fuel may be determined from the frequency of the pressure wave, the speed of sound may be correlated with a molecular weight of the gaseous fuel using a polynomial function that relates speed of sound with ideal gas molecular weights, and the specific gravity of the gaseous fuel may be estimated from the molecular weight of the gaseous fuel. The specific gravity values provided by the methods and systems disclosed herein may improve the accuracy of various operation parameters of the engine, such as the gaseous fuel flow rate and the engine air/fuel ratio. It is expected that the technology disclosed herein may find wide industrial applicability in a wide range of areas such as, but not limited to, automotive and aerospace applications, power generation applications, and fuel extraction applications.

What is claimed is:

1. A method for estimating a specific gravity of a gaseous fuel, the gaseous fuel powering an engine and the engine including a cylinder, a gas valve configured to supply an intake port of the cylinder with the gaseous fuel, a gas rail configured to deliver the gaseous fuel to the gas valve, and a microprocessor adapted to perform the method, said method comprising:
    establishing a pressure wave in the gas rail by opening and closing the gas valve, the pressure wave traveling at a speed of sound in the gaseous fuel;
    determining a frequency of the pressure wave in the gas rail; and
    estimating the specific gravity of the gaseous fuel based on the frequency of the pressure wave.

2. The method of claim 1, wherein estimating the specific gravity of the gaseous fuel based on the frequency of the pressure wave comprises:

determining the speed of sound in the gaseous fuel based on the frequency of the pressure wave;
estimating a specific gas constant for the gaseous fuel based on the speed of sound in the gaseous fuel;
estimating a molecular weight of the gaseous fuel based on the specific gas constant; and
estimating the specific gravity of the gaseous fuel based on the molecular weight of the gaseous fuel and a molecular weight of air.

3. The method of claim 1, wherein estimating the specific gravity of the gaseous fuel based on the frequency of the pressure wave comprises comparing the frequency of the pressure wave with a calibration map that correlates gaseous fuel pressure wave frequencies with specific gravities.

4. The method of claim 1, wherein estimating the specific gravity of the gaseous fuel based on the frequency of the pressure wave comprises:
determining the speed of sound in the gaseous fuel based on the frequency of the pressure wave;
calculating a molecular weight of the gaseous fuel based on the speed of sound in the gaseous fuel using a polynomial function relating speed of sound in gaseous fuels with gaseous fuel molecular weights; and
estimating the specific gravity of the gaseous fuel based on the molecular weight of the gaseous fuel and a molecular weight of air.

5. The method of claim 1, wherein the engine is a multi-fuel engine and includes a plurality of cylinders, and wherein the method further comprises running one of the cylinders in gas mode in which the cylinder is supplied with the gaseous fuel as a primary fuel source prior to establishing the pressure wave in the gas rail.

6. The method of claim 5, wherein the engine is a V-engine, and wherein running one of the cylinders in gas mode comprises running one cylinder in each bank in gas mode.

7. The method of claim 2, wherein determining the specific gas constant for the gaseous fuel based on the speed of sound is performed by solving the equation $c=\sqrt{kR_sT}$ for $R_s$, where c is the speed of sound in the gaseous fuel, k is a specific heat ratio of the gaseous fuel, T is temperature, and $R_s$ is the specific gas constant of the gaseous fuel.

8. The method of claim 7, wherein determining the molecular weight of the gaseous fuel based on the specific gas constant is performed using the equation $MW_G=R/R_s$, where $MW_G$ is the molecular weight of the gaseous fuel, R is the ideal gas constant, and $R_s$ is the specific gas constant for the gaseous fuel.

9. The method of claim 8, wherein estimating the specific gravity of the gaseous fuel based on the molecular weight of the gaseous fuel and the molecular weight of air is performed using the equation $SG_{Ge}=MW_G/MW_{air}$, where $SG_{Ge}$ is the specific gravity of the gaseous fuel, $MW_G$ is the molecular weight of the gaseous fuel, and $MW_{air}$ is the molecular weight of air.

10. An engine powered by a gaseous fuel having an unknown specific gravity, comprising:
at least one cylinder having a combustion chamber disposed therein;
a piston positioned for displacement within the cylinder;
an intake port configured to deliver a mixture of air and the gaseous fuel to the cylinder;
a gas valve configured to regulate a gas mass flow into the intake port;
a gas rail configured to supply the gas valve with the gaseous fuel, the gas valve being configured to generate a pressure wave in the gas rail when the gas valve is opened and closed;
a pressure sensor in the gas rail configured to detect the pressure wave; and
a specific gravity estimation module configured to determine a frequency of the pressure wave detected by the pressure sensor, and to estimate the specific gravity of the gaseous fuel based on the frequency of the pressure wave.

11. The engine of claim 10, wherein the specific gravity estimation module further comprises:
a speed of sound module configured to determine a speed of sound in the gaseous fuel based on the frequency of the pressure wave;
a specific gas constant module configured to estimate a specific gas constant of the gaseous fuel based on the speed of sound in the gaseous fuel;
a molecular weight module configured to estimate a molecular weight of the gaseous fuel based on the specific gas constant of the gaseous fuel; and
a specific gravity module configured to estimate the specific gravity of the gaseous fuel based on the molecular weight of the gaseous fuel and a molecular weight of air.

12. The engine of claim 10, wherein the specific gravity estimation module is configured to estimate the specific gravity of the gaseous fuel by comparing the frequency of the pressure wave with a calibration map that correlates gaseous fuel pressure wave frequencies with specific gravities.

13. The engine of claim 10, wherein the specific gravity estimation module further comprises:
a speed of sound module configured to determine a speed of sound in the gaseous fuel based on the frequency of the pressure wave;
a molecular weight module configured to calculate a molecular weight of the gaseous fuel based on the speed of sound in the gaseous fuel using a polynomial function relating speed of sound in gaseous fuels with gaseous fuel molecular weights; and
a specific gravity module configured to estimate the specific gravity of the gaseous fuel based on the molecular weight of the gaseous fuel and a molecular weight of air.

14. The engine of claim 10, wherein the engine is a multi-fuel engine having a plurality of cylinders, and wherein the specific gravity estimation module further includes a learning mode module configured to set one of the cylinders in gas mode in which the cylinder is supplied with the gaseous fuel as a primary fuel source.

15. The engine of claim 14, wherein the engine is a V-engine, and wherein the learning mode module is configured to set one of the cylinders in each bank of the V-engine in gas mode.

16. The engine of claim 14, wherein the engine is an in-line engine, and wherein the learning mode module is configured to run one of the cylinders in a row of cylinders in gas mode.

17. The engine of claim 11, wherein the specific gas constant module is configured to determine the specific gas constant of the gaseous fuel by solving the equation $c=\sqrt{kR_sT}$ for $R_s$, where c is the speed of sound in the gaseous fuel, k is a specific heat ratio of the gaseous fuel, T is temperature, and $R_s$ is the specific gas constant for the gaseous fuel.

18. The engine of claim 17, wherein the molecular weight determination module is configured to determine the molecular weight of the gaseous fuel using the equation $MW_G=R/R_s$, where $MW_G$ is the molecular weight of the gaseous fuel, R is the ideal gas constant, and $R_s$ is the specific gas constant for the gaseous fuel.

19. The engine of claim 18, wherein the specific gravity module is configured to estimate the specific gravity of the gaseous fuel using the equation $SG_{Ge}=MW_G/MW_{air}$, where $SG_{Ge}$ is the specific gravity of the gaseous fuel, $MW_G$ is the molecular weight of the gaseous fuel, and $MW_{air}$ is the molecular weight of air.

20. A method for estimating a specific gravity of a gaseous fuel, the gaseous fuel powering a dual fuel engine configured to run on at least the gaseous fuel and diesel fuel, the engine including a plurality of cylinders, an intake port associated with each one of the cylinders, a gas valve associated with each one of the intake ports and configured to supply the intake port with the gaseous fuel, a gas rail configured to supply the gas valves with the gaseous fuel, and a microprocessor adapted to perform the method, said method comprising:
 running one of the cylinders in gas mode in which the cylinder is supplied with the gaseous fuel as a primary fuel source;
 running the remaining cylinders in diesel mode in which the diesel fuel is used as a sole fuel source;
 establishing a pressure wave in the gas rail by opening and closing the gas valve associated with the cylinder running in gas mode, the pressure wave traveling at a speed of sound in the gaseous fuel;
 determining a frequency of the pressure wave in the gas rail; and
 estimating the specific gravity of the gaseous fuel based on the frequency of the pressure wave.

* * * * *